United States Patent
Rogier

(10) Patent No.: US 11,235,136 B2
(45) Date of Patent: *Feb. 1, 2022

(54) SWABABLE VALVE WITH CURVILINEAR VALVE STEM

(71) Applicant: Halkey-Roberts Corporation, St. Petersburg, FL (US)

(72) Inventor: Stephen J. Rogier, Palm Harbor, FL (US)

(73) Assignee: Halkey-Roberts Corporation, St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/001,137

(22) Filed: Aug. 24, 2020

(65) Prior Publication Data

US 2021/0069485 A1    Mar. 11, 2021

Related U.S. Application Data

(63) Continuation-in-part of application No. 15/295,545, filed on Oct. 17, 2016, now Pat. No. 10,751,523.

(51) Int. Cl.
*A61M 39/24* (2006.01)
*A61M 39/26* (2006.01)

(52) U.S. Cl.
CPC ............ *A61M 39/24* (2013.01); *A61M 39/26* (2013.01); *A61M 2039/2426* (2013.01); *A61M 2039/261* (2013.01)

(58) Field of Classification Search
CPC .................. A61M 39/24; A61M 39/26; A61M 2039/2426; A61M 2039/261; F16K 25/005; F16K 3/28

USPC ..... 251/149.1; 604/256, 905, 167.02, 167.04
See application file for complete search history.

(56) References Cited

U.S. PATENT DOCUMENTS

| | | | | |
|---|---|---|---|---|
| 4,649,904 A | ‡ | 3/1987 | Krauter | A61B 1/00137 285/331 |
| 5,251,873 A | ‡ | 10/1993 | Atkinson | A61M 39/045 251/149.1 |
| 5,295,658 A | ‡ | 3/1994 | Atkinson | A61M 39/045 251/149.1 |
| 5,501,426 A | ‡ | 3/1996 | Atkinson | A61M 39/045 251/14 |

(Continued)

FOREIGN PATENT DOCUMENTS

WO    PCTUS9210367    ‡  6/1993

*Primary Examiner* — John Bastianelli
(74) *Attorney, Agent, or Firm* — Stefan V. Stein

(57) ABSTRACT

A swabable valve (10) comprising a valve stem (100) that collapses into a valve body (12), said valve body (12) including a generally cylindrical reduced diameter section (18) having a generally circular rim, said valve stem (100) having a generally cylindrical reduced diameter portion (38) that extends fully into said cylindrical reduced diameter section (18) of said valve body (12), said cylindrical reduced diameter portion (38) including a through-slit (52) that opens when said valve stem (100) collapses into said valve body (12), said valve stem (100) having a concave curvilinear surface (102) that is substantially flush with said circular rim of said cylindrical reduced diameter section (18) of said valve body (12) when said valve stem (100) is not collapsed into said valve body (12); said concave curvilinear upper surface (102) of said valve stem (100) extending rim-to-rim within said cylindrical reduced diameter section (18) of said valve body (12).

10 Claims, 11 Drawing Sheets

(56) References Cited

U.S. PATENT DOCUMENTS

| | | | | |
|---|---|---|---|---|
| 5,699,821 A | ‡ | 12/1997 | Paradis | A61M 39/02 137/1 |
| 5,807,348 A | ‡ | 9/1998 | Zinger | A61M 39/045 604/246 |
| 5,814,024 A | ‡ | 9/1998 | Thompson | A61M 39/045 251/149.1 |
| 5,833,674 A | ‡ | 11/1998 | Turnbull | A61M 39/045 604/53 |
| 5,957,898 A | ‡ | 9/1999 | Jepson | A61M 39/045 128/91 |
| 6,036,171 A | ‡ | 3/2000 | Weinheimer | A61M 39/26 251/14 |
| 6,079,432 A | ‡ | 6/2000 | Paradis | A61M 39/26 137/1 |
| 6,089,541 A | ‡ | 7/2000 | Weinheimer | A61M 39/26 251/14 |
| 6,127,320 A | ‡ | 10/2000 | van Ooij | A61M 39/045 508/138 |
| 6,162,251 A | ‡ | 12/2000 | Kredovski | A61F 2/02 623/11.11 |
| 6,171,287 B1 | ‡ | 1/2001 | Lynn | A61M 39/02 251/149 |
| 6,651,956 B2 | ‡ | 11/2003 | Miller | A61M 39/045 251/14 |
| 8,221,363 B2 | | 7/2012 | Jepson | |
| 2004/0006330 A1 | ‡ | 1/2004 | Fangrow, Jr. | A61M 39/02 604/533 |
| 2005/0261637 A1 | ‡ | 11/2005 | Miller | A61M 39/26 604/25 |
| 2008/0000982 A1 | | 1/2008 | Knowles et al. | |
| 2008/0009822 A1 | ‡ | 1/2008 | Enerson | A61J 1/2096 604/41 |
| 2010/0249725 A1 | * | 9/2010 | Cote, Sr. | A61M 39/26 604/249 |
| 2015/0014193 A1 | | 1/2015 | Zeier | |
| 2015/0141937 A1 | ‡ | 5/2015 | Bonaldo | A61M 39/26 604/25 |

\* cited by examiner

‡ imported from a related application

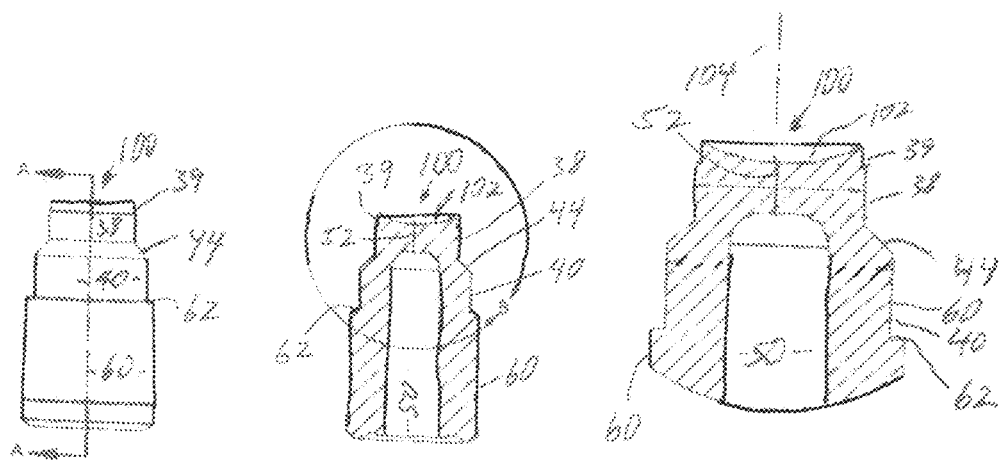
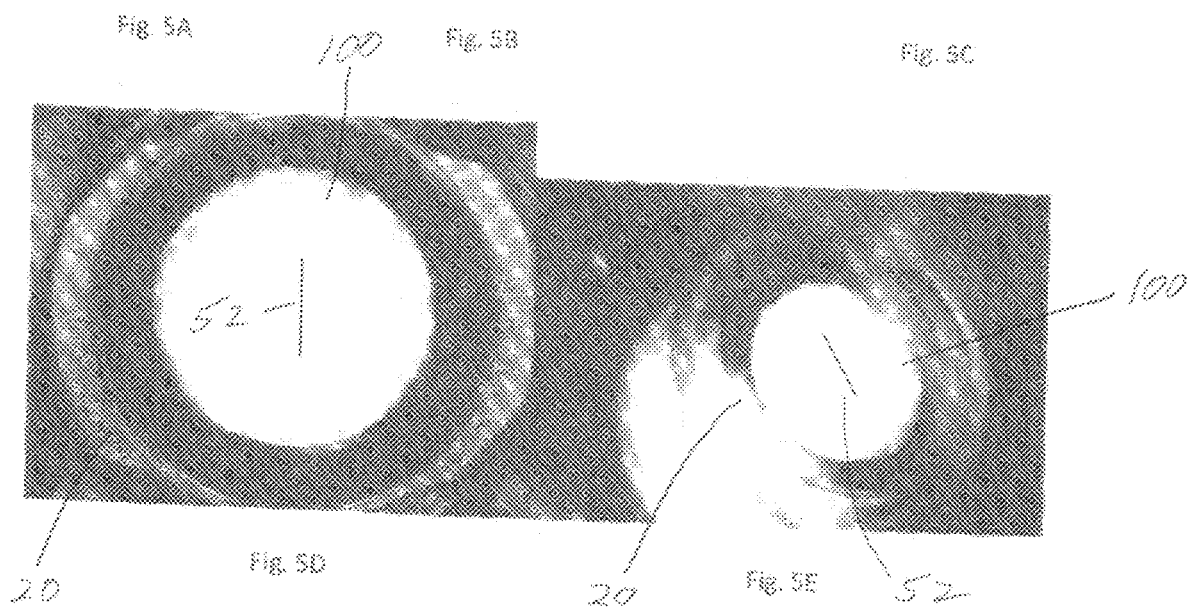

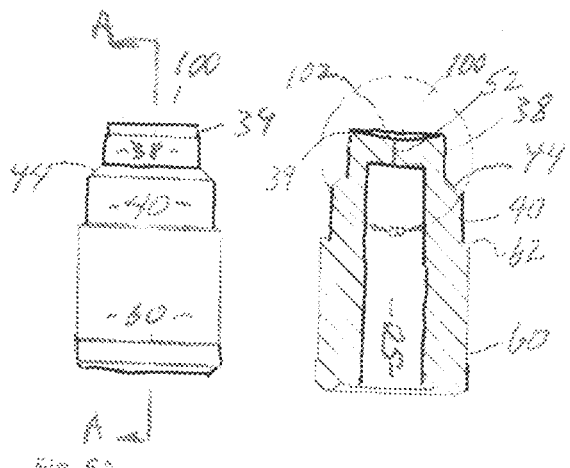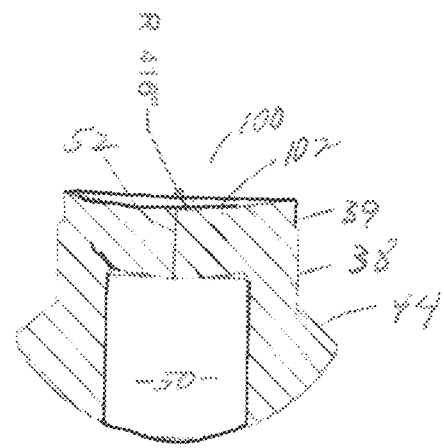
Fig. 6A  Fig. 6B  Fig. 6C
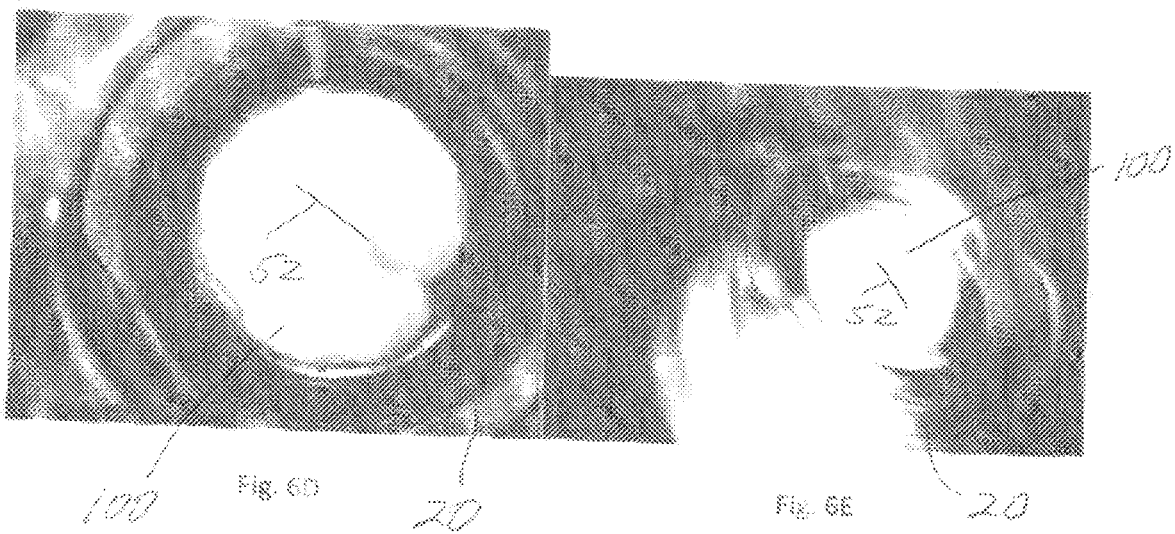
Fig. 6D  Fig. 6E

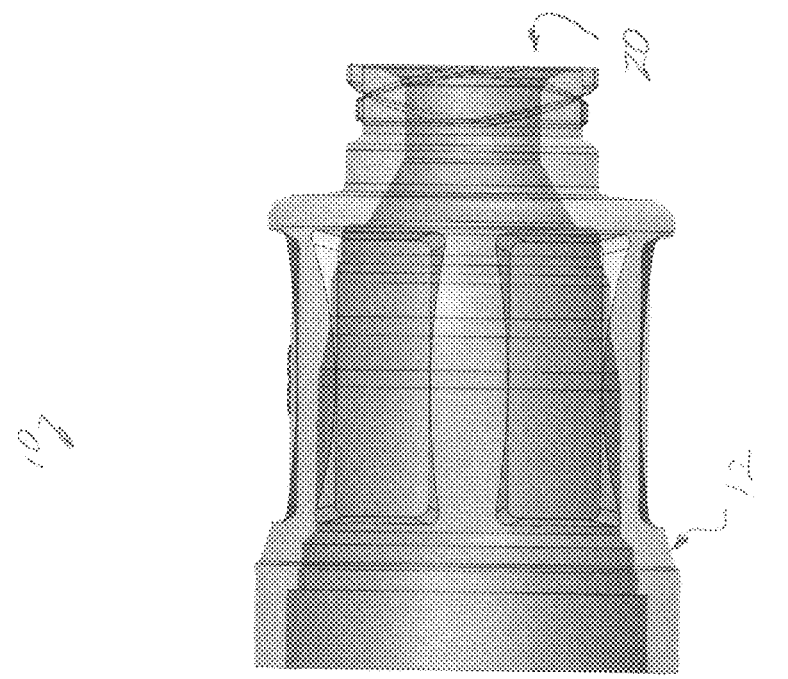
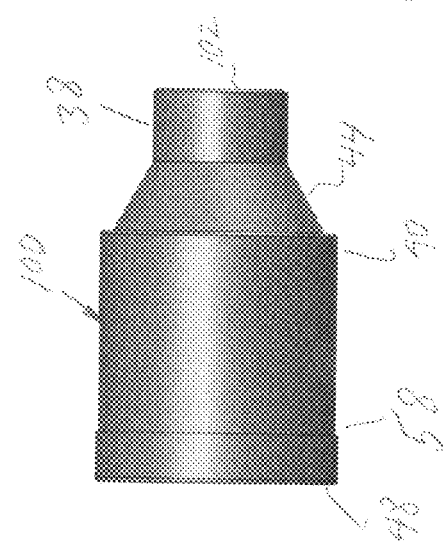
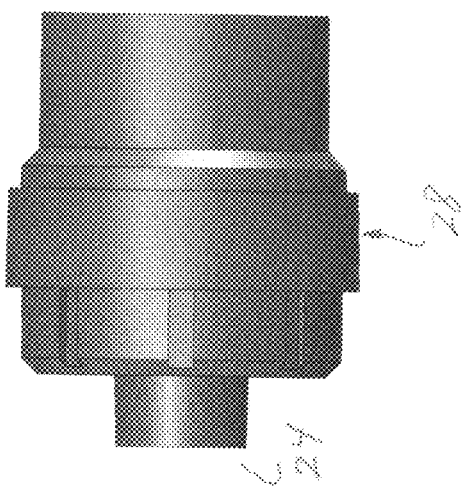
Fig. 7

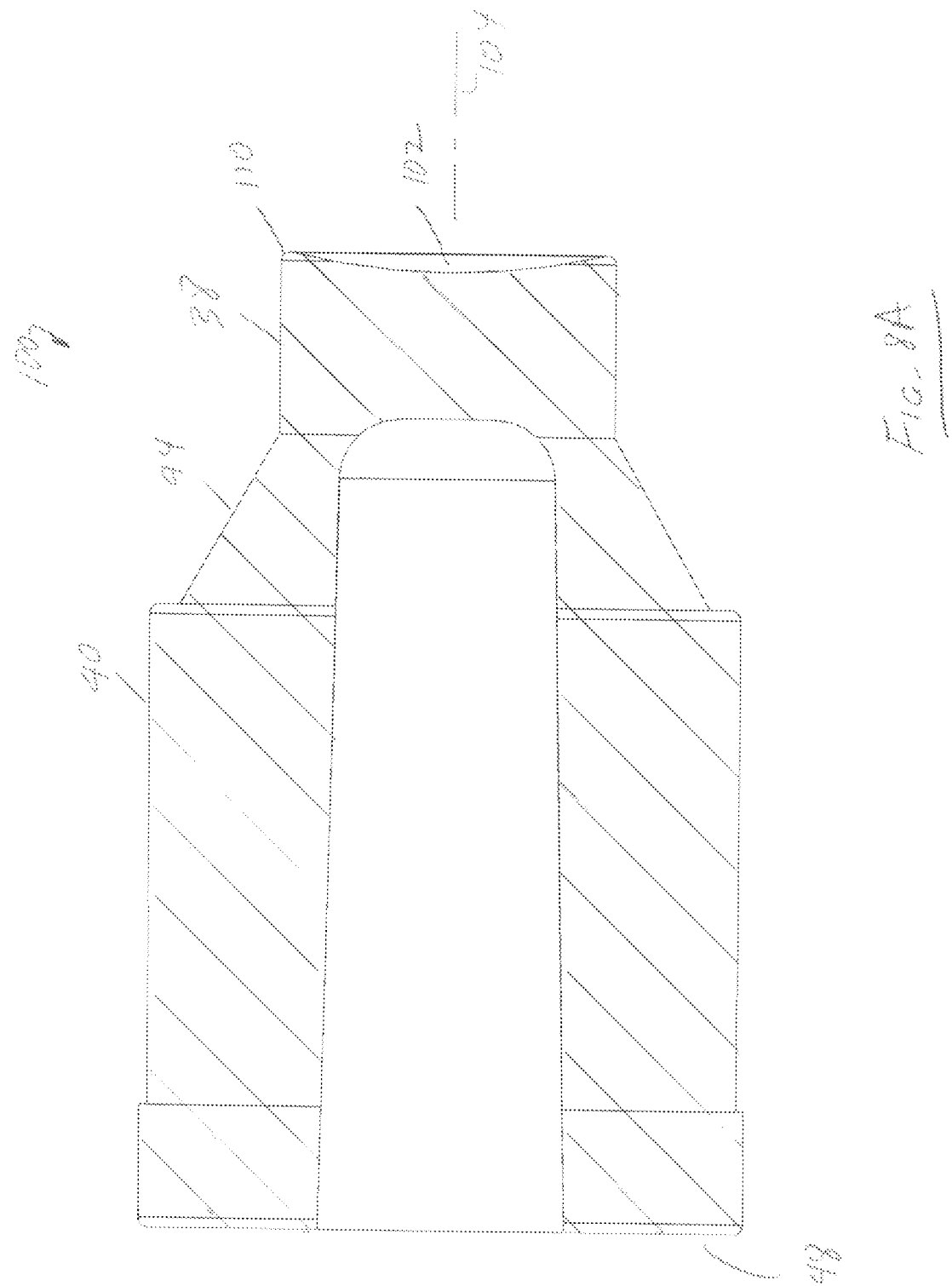

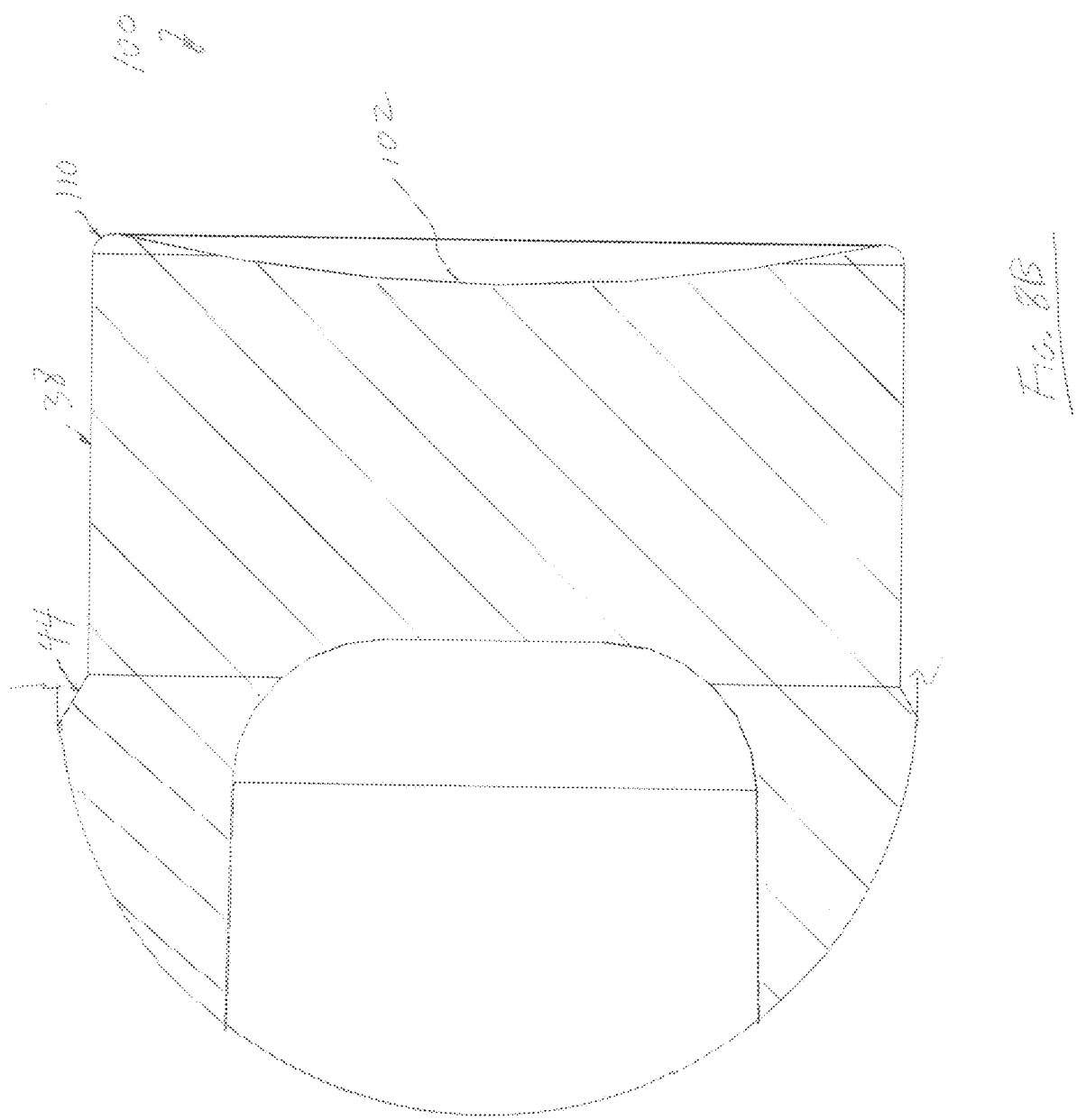

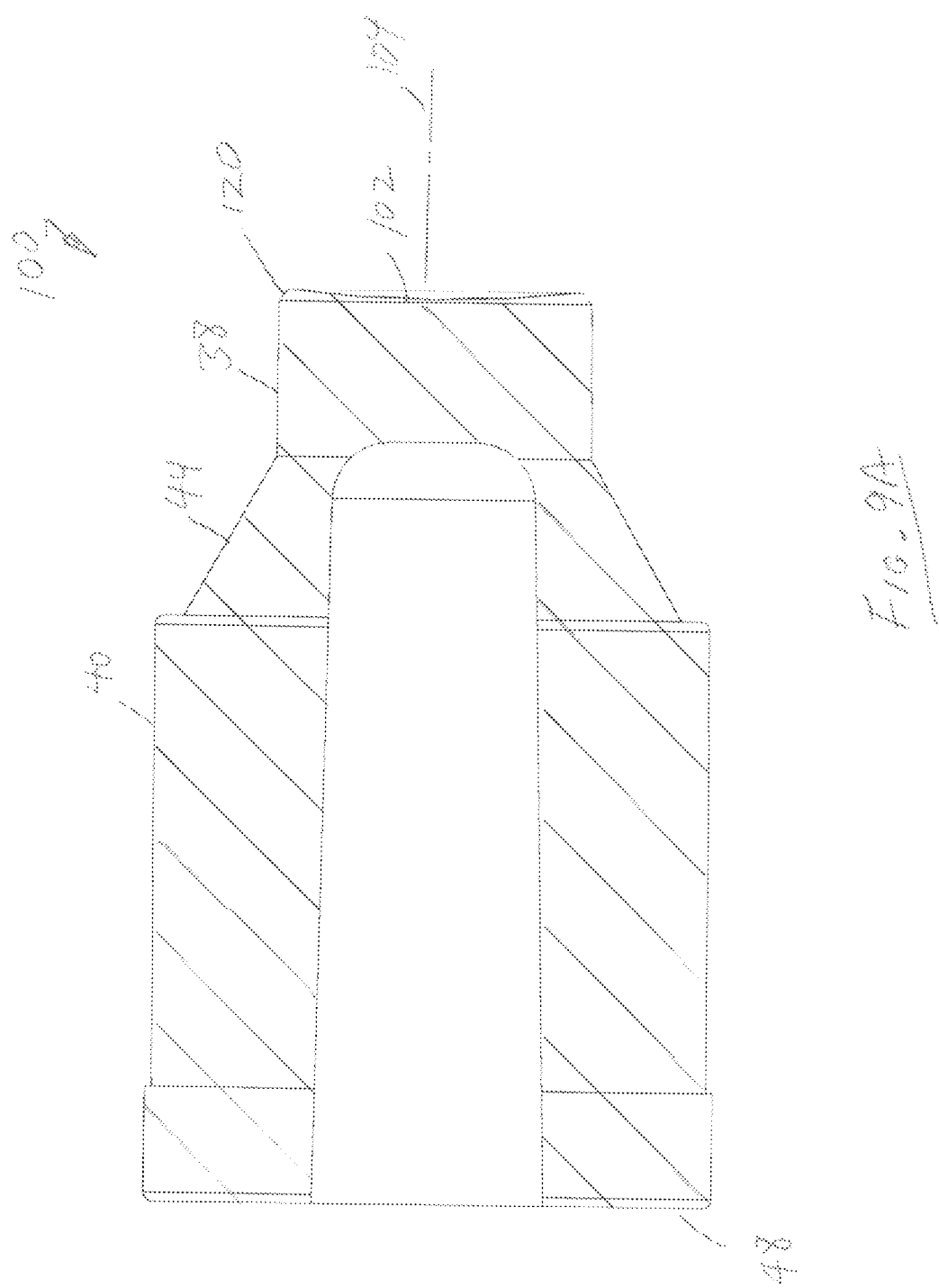

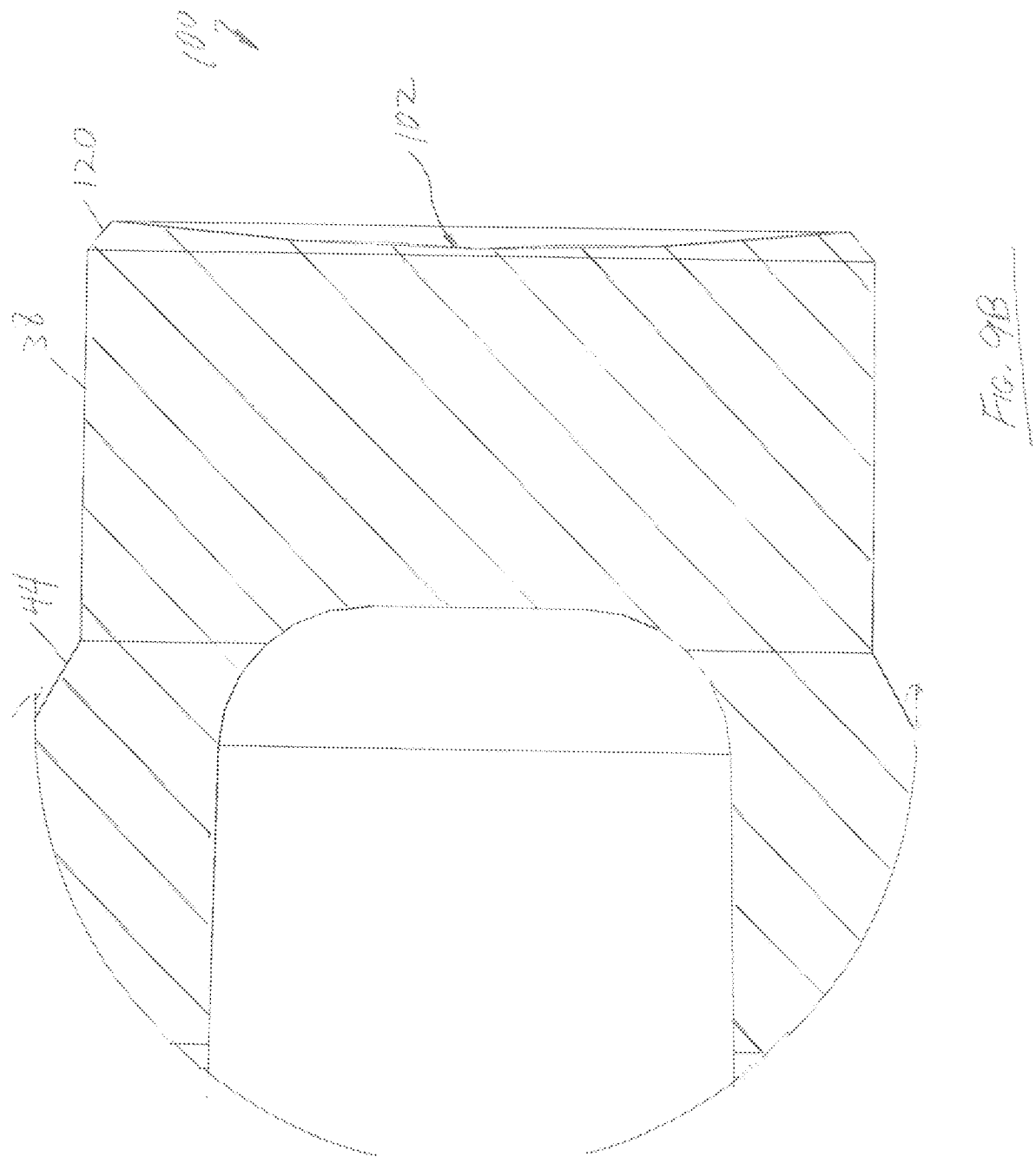

SWABABLE VALVE WITH CURVILINEAR VALVE STEM

CROSS-REFERENCE TO RELATED APPLICATIONS

This application is a continuation-in-part application of Ser. No. 15/295,545 filed Oct. 18, 2016 issued as U.S. Pat. No. 10,751,523 on Aug. 25, 2020, which claims the benefit of provisional application No. 62/243,036, filed Oct. 17, 2015, the disclosures of which are hereby incorporated by reference herein.

BACKGROUND OF THE INVENTION

Field of the Invention

This invention relates to Luer activated valves. More particularly, invention relates to a swabable valve having a swabable valve stem.

Description of the Background Art

Presently there exist numerous types of swabable valves for intravenous (IV) lines, containers and the like that include an internal elastomeric valve stem having a through-slit that is normally-closed within a valve body to preclude fluid flow through the valve. When accessed by an access device, such as the tip of a male Luer fitting on the end of a syringe or other IV component, the tip of the access device forces the valve stem inwardly into the valve body upon which the tip enters into the slit to open the valve stem allowing fluid flow from the access device, through its tip and then through the now forced-open slit. Upon removal of the tip of the access device from the valve, the elastomeric properties of the valve stem resiliently move the valve stem outwardly to return to its normally-closed position within the valve body.

Representative patents and patent applications that teach swabable valves having elastomeric valve stems owned by the assignee of this application are disclosed in U.S. Pat. Nos. 6,651,956, 6,089,541 and 6,036,171 and U.S. Published Patent Applications 2015/0141937, 2008/0009822 and 2005/0261637, the disclosures of which are hereby incorporated herein.

As described in U.S. Pat. No. 6,651,956, the valve 10 shown in FIGS. 1-2 includes a substantially tubular valve body 12 having a central axial bore 14 forming an enlarged diameter section 16 and a reduced diameter section 18. The bore 14 defines a first open end 20 for receiving a male valve component or instrument (hereinafter generally referred to as an access device) 22, such as a needleless syringe having a Luer tip, and a second open end 24 for communication with a fluid line (not shown) or other another access device. Preferably, the valve body 12 is comprised of a relatively rigid, durable material such as a thermoplastic material (e.g., a polycarbonate).

For ease of assembly, the valve body 12 may be formed of two portions, a front body portion 26 and a rear body portion 28, which are ultrasonically sealed together at a weld joint 30 to provide the continuous valve body 12. Ultimately, it should be appreciated that the location of the joint 30 is not imperative, and that the valve body 12 need not even be formed of two separate pieces that are connected together, but may be formed of even more pieces or may be formed as a unitary, single-bodied piece. As an alternative to the weld joint 30, a snap joint or a glued joint may be provided between the front portion 26 and the rear portion 28 of the valve body 12. As shown, preferably the shape of the housing 12 is such that its external surface provides a generally convex-like shape, wherein a shoulder cross sectional diameter at a proximal end is larger than the cross sectional diameter in the middle of the housing (i.e., the front portion 26 is wider at shoulder 21 than it is in the middle of the valve 10), thus facilitating secure handling of the valve 10.

The rear portion 28 of the valve body 12 comprises an axial passageway preferably configured as a male Luer fitting for receiving an access device having corresponding female Luer fitting (not shown). Alternatively, the rear portion 28 may be configured for direct engagement with a fluid line such as a tube. In fact, there are many alternatives for the shape and configuration of the rear end of the valve.

Within the valve body 12 is a valve stem 32. Preferably, the stem 32 is comprised of silicone, but the stem 32 may instead be formed of some other resilient elastomer material, such as natural rubber, a thermoplastic elastomer, or a thermoplastic rubber. As best shown in FIGS. 3A, 3B and 3C, the stem 32 preferably has a generally conical front body portion 34 and a generally cylindrical rear body portion 36. Both the front body portion 34 and rear body portion 36 have generally circular cross-sectional profiles, and the valve body 12 is correspondingly shaped. The front body portion 34 of the stem 32 includes a generally cylindrical reduced diameter portion 38 having (having a front end 46), a generally cylindrical increased diameter portion 40 and a connected by a generally frustro-conical portion 44 positioned between the cylindrical portions 38 and 40.

The rear body portion 36 of the stem 32 is preferably substantially cylindrical to provide strong axial compression resistance, and terminates at a blunt or flat rear end 48, generally opposite front end 46. The stem 32 has a central axial fluid passageway 50 therethrough which defines, at one end of the passageway 50, a through-slit 52 in the front end 46 of the stem 32 and defines, at the other end of the passageway, an opposite, rear end opening 54. Preferably the rear end 54 of the stem 32 sealingly aligns with an internal surface of the valve body 12 thus providing a smooth fluid flow path between the fluid passageway 50 in the stem 32 and the valve body 12 for carrying a liquid, air or other fluid within the valve 10. Preferably, the sidewall of the stem 32 extends from one end 46 of the stem 32 to the other 48.

An optional annular notch 39 extends about the annular periphery of the cylindrical portion 38 such that it functions as a relief feature because it allows portion 38 to be compressed to more tightly seal the slit 52 closed and to seal the frustro-conical portion 44 within the corresponding portion 65 of the valve body 12, thereby greater resistance to fluid back pressure.

An optional annular groove 58 provides a point of weakness on the exterior surface 60 of the valve stem 32. The groove 58 is configured to provide that, when the male access device 22 is engaged with the valve 10, the valve stem 32 buckles or expands generally outwardly, at the groove 58, thereby providing increased flow volume within the valve stem 32. The increased flow volume provides less flow resistance.

While the rear end opening 54 of the stem 32 is always open, in one prior art embodiment the slit 52 in the front portion 34 of the stem 32 is normally closed even when the valve stem 32 is not compressed within the valve body 12 and in another prior art embodiment, the slit 52 is normally open when the valve stem 32 is not compressed within the valve body 12.

When an access device 22 is engaged in the slit 52 of the valve stem 32, the slit 52 seals against the outer surface of the access device 22 and the stem 32 moves inwardly into the valve body 12. When the slit 52 is opened, fluid flow is allowed through the stem 32, to or from the access device 22. The structure of the valve 10 is such that when the valve 10 is actuated, fluid can flow in either direction through the valve 10. As the access device 22 is being removed from the slit 52 in the end 46 of the stem 32, the slit 52 closes shut, and this prevents fluid leak upon further removal of the access device 22. Also, the stem configuration is such that the slit 52 swabs or cleans the tip 56 of the access device 22 as the tip 56 is being removed.

A shoulder 62 is provided on the stem 32, generally at the juncture of the generally increased-diameter portion 34 and the generally cylindrical rear body portion 36. The shoulder 62 could engage a corresponding shoulder 64 in the valve body 12, thereby forming a point of sealed contact therebetween. This point of sealed contact remains regardless of whether an access device 22 is engaged with the valve 10 or not (see FIG. 2). Furthermore, when an access device 22 is not engaged with the valve 10, generally the entire side surface of the front portion 34 of the stem 32 sealingly engages internal surface 65 of the valve housing 12. This sealed engagement results from the fact that the configuration of the front body portion 26 of the valve body 12 is generally about the same as that of the respective reduced-diameter, frustro-conical 44, and and increased-diameter portions 38, 44 and 40 of the stem 32.

The end 48 of the stem 32 is also seated against a shoulder 66 within the valve body 12, such as on the interior of the back portion 28, thereby forming another point of sealed contact. To provide for additional sealed contact, the end 48 of the stem 32 is provided with both a flat portion 68 adjacent the end 54 and a lip 70 which protrudes from the end 54. While the lip 70 and portion 68 seals against the shoulder 66 within the valve body 12, the portion 36 seals against an adjacent internal side wall 25 within the valve body 12 thereby providing essentially two sealing contact surfaces between the end 48 of the stem 32 and the valve body 12, thereby preventing fluid from entering or leaking from the axial passageway 72 into the neutral space 74 between the stem 32 and the valve body 12. Hence, overall, there are always essentially three points of sealing contact between the valve stem 32 and the interior of the valve body 12 (i.e., a point of sealed contact between shoulder 62 and shoulder 64, and two points of sealed contact between the end 48 of the stem 32 and the interior of the valve body 12). Still further, as discussed above, preferably the configuration of the front portion 26 of the valve body 12 is generally about the same as that of the front portion 34 of the stem 32, thereby providing that the surface of the front portion 34 of the stem 32 generally seals against the interior surface 65 of the valve body 12. One having ordinary skill in the art may recognize still other ways in which to provide points of sealed contact between the stem 32 and the valve body 12. Providing sealed contact between the stem 32 and the valve body 12 is important in order to prevent fluid from entering or leaking into the neutral space 74 between the stem 32 and the valve body 12 from the axial passageway 50.

When there is no access device engaged with the valve, the slit 52 in the end 46 of the valve stem 32 is fully closed, and the end 46 of the valve stem 32 is generally flush with the bottom of the front concave area 23 of the valve body 12, thereby facilitating sterilization of the end 46 of the stem 32 by swabbing with an alcohol wipe or swab between the stem 32 and the valve body 12. This feature is important in medical applications where bacteria growth is to be avoided.

Optionally, a concave area 23 formed in the first opened end 20 of the valve body 12 may be provided to guide an access device 22 into the valve body 12.

The stem 32 is preferably configured such that, when an access device 22 is not engaged with the valve 10, the valve stem 32 naturally rests in the position shown in FIG. 1. However, means may be provided for urging the end 46 of the stem 32 towards the end 20 of the valve body 12. Particularly, a compression spring (not shown) may be provided in the neutral space 74 between the stem 32 and the valve body 12.

While a compression spring may be provided between the stem 32 and the valve body 12, it is preferred that the rear body portion 36 of the stem 32 be provided as having a thick wall and being robust enough to provide a sufficient spring rate or force in order to urge the end 48 of the stem 32 towards the first end 20 of the valve body 12.

Operation of the valve 10 will now be described in connection with engagement of an access device 22 therewith. As mentioned, the access device 22 to be engaged with the valve 10 may be a needleless syringe having a male Luer tip. Before the access device 22 is engaged with the valve 10, the valve 10 is in the condition shown in FIG. 1. At that time, the slit 52 is closed and hermetically sealed. Additionally, as described above, the stem 32 is sealed against the valve body 12 at various points (i.e., vis-a-vis end 48, shoulder 62, and the entire surface of the front portion 34 of the stem 32).

When the tip 56 of the access device 22 is first brought into engagement with the slit 52 in the front end 46 of the stem 32, the slit 52 initially resists the insertion thereof. However, as the tip 56 of the access device 22 is further pushed or engaged into the slit 52 to move the stem 32 inwardly, the slit 52 eventually deforms or opens to allow entry of the tip 56 of the access device 22 into the slit 52, as shown in FIG. 2, and due to the resiliency of stem 32, a tight hermetic seal is formed between the stem 32 and the tip 56 of the access device 22. The engagement of the tip 56 with stem 32 serves to further compress the stem 32 and further enhance the internal seals, especially at end 54.

As the tip 56 of the access device 22 is further pushed into the slit 52 in the stem 32, the end 46 of the stem 32 is pushed more inwardly into the valve body 12, and, as shown in FIG. 2, the valve stem 32 buckles or expands generally outwardly, at the notch 58. End 46 of stem 32 collapses and folds inward into the cavity 50, approximately around a fulcrum point located at the area of minimal wall thickness. The slit 52 fully opens and fluid flow is allowed through the stem 32, to or from the access device 22. As the access device 22 is being removed from the slit 52 in the end 46 of the stem 32, the slit 52 closes shut and seals, thus preventing a fluid leak. Additionally, the stem 32 wipes or swabs the tip 56 clean upon removal.

A female thread or Luer lock thread 76 may be provided on the valve body 12 near the end 20 thereof for engagement with a corresponding male Luer lock thread 78 on the access device 22, or other corresponding structure(s) may be provided between the valve 10 and the access device 22 for engagement therebetween. It is preferable to provide the described Luer lock threads or some other engagement structure because the engagement between the valve 10 and the access device 22 helps to align the access device 22 while providing a mechanical advantage to overcome the resistance by the slit 52 to expanding and accommodating the tip 56 of the access device 22. However, it should be pointed out that threaded engagement between the valve body 12 and the access device 22 is not necessary to keep the tip 56 of the access device 22 and the slit 52 of the stem 32 engaged because the grip or the frictional engagement between the tip 56 of the access device 22 and section 18 of the valve body 12, plus engagement of the slit 52 around the tip 56, is sufficient to hold the access device 22 and the valve 10 in engagement. Nevertheless, it may be desirable to provide the above-described Luer lock threads 76 and 78 on the access device 22 and valve body 12, respectively, or some other engagement structure, when large separation forces will be present therebetween. This, of course, will depend on the application in which the valve 10 is used.

After the tip 56 of the access device 22 is engaged with the slit 52, fluid may be injected or withdrawn via the tip 56 through the stem 32, that is to say, the access device 22 may suction or inject fluid through the stem 32. As the fluid flows, no fluid enters the neutral space 74 between the stem 32 and the valve body 12. Therefore, bacteria growth in the neutral space 74 is precluded.

Consideration is now directed to what occurs upon disengagement of the access device 22 from the valve 10. As the tip 56 of the access device 22 is initially withdrawn from the slit 52 in the end 46 of the stem 32, the stem 32, due to its inherent resiliency, is urged toward the end 20 of the valve body 12. As a result of this bias of the stem 32 toward the tip 56, the slit 52 in the stem 32 and adjacent internal stem walls wipe or swab the tip 56 virtually free of fluid as the tip 56 is being withdrawn. In medical applications, this can reduce the waste of expensive injectable solutions and minimize unintended, undesired human exposure to the fluid, which may be contaminated or be a bio hazardous fluid.

The above-described valve 10 provides several advantages over the prior art. For example, the neutral space 74 is sealed from any fluid flow. Therefore, there is no leaking of fluid thereinto, and a compression spring, if provided between the stem 32 and the valve body 12, is not exposed to the flowing fluid. Also, the tip 56 of the access device 22 is wiped virtually free of fluid upon the tip 56 being withdrawn from the valve 10. Additionally, the valve 10 provides no perceptible areas for bacterial growth. Still further, the stem 32 is configured with the annular notch 39 to achieve relatively flat and wrinkle free top surface at the end 46. All the components preferably have generally circular cross sectional geometry and therefor there is no need for precise part orientation during assembly of the valve, allowing for reliable high-speed manufacture. Still further, the stem 32 is configured to buckle when the tip 56 of an access device 22 is inserted in the slit 52 in the end 46 of the stem 32, and this provides increased internal flow volume and less resistance to fluid flow. Many more advantages are provided by the present invention and have been previously described herein. One having ordinary skill in the art may readily realize even more advantages.

As described above and shown in FIGS. 3A-3E, at rest (i.e., not installed in the valve body 12), the exposed upper surface 46 of the stem 32 comprises a generally flat configuration. As shown in FIG. 3F, when the valve stem 32 is compressed after being installed within the valve body 12, the exposed upper surface 46 becomes slightly convex. Valve stems 32 of this configuration have been successfully commercialized by the assignee of U.S. Pat. No. 6,651,956 for many years.

Historically, valve stem 32 has been composed of silicone having a durometer of about 40. It is noted that during cutting of the through-slit 52, the cutting blade is usually lubricated to minimize tearing while cutting and to minimize healing of the slit when the assembled valve 10 is later sterilized. It is also noted that during assembly, the valve stem 32 is typically lubricated to enhance its ability to reduce the coefficient of friction between its front conical portion 34 and the enlarged and reduced diameter portions 16 and 18 of the valve body 12, thereby allowing the valve stem 32 to more freely collapse when being engaged by an access device 22 and to then return to its at rest position when disengaged.

The manufacturer's Instructions For Use (IFU) has required that the valve 10 be accessed by the access device 22 co-axially such that the tip of the access device 22 pushes the stem 32 axially inwardly of the body 12 to uniformly collapse the stem 32. Unfortunately, however, there have been instances wherein if the tip of the access device is pushed into valve 10 at an acute angle (not co-axially in accordance with the IFU), the valve stem 32 after collapsing may become lodged inwardly of the valve body 12. FIGS. 4A and 4B illustrate an inwardly-lodged valve stem 32 in the valve body 12. The above-described lubrication of the slit in the valve stem reduced the frequency of lodged valve stems even when the valve is accessed contrary to the IFU; however, incidents of lodged valve stems 32 are occasionally reported.

Therefore, an object of this invention to provide an improvement which overcomes the aforementioned inadequacies of the prior art devices and provides an improvement which is a significant contribution to the advancement of the swabable valve art.

Another object of this invention is to provide a swabable valve including a valve stem that cannot be lodged within the valve body even when intentionally accessed at an acute angle contrary to the IFU.

Another object of this invention is to provide a valve stem having a concave, curvilinear surface that extends rim-to-rim at a depth sufficient to preclude lodging of the valve stem within the valve body.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, the invention comprises a swabable valve having a collapsible valve stem with an exposed concave curvilinear front surface. Preferably, the concave curvilinear surface extends from rim-to-rim of the valve stem. More preferably, the concave curvilinear surface comprises a radius that is sufficient to prevent the valve stem from becoming lodged within the valve body upon collapsing, thereby assuring that the collapsed valve stem will return to its closed position with the concave curvilinear surface substantially flush with the end of the valve. Still more preferably, the radius of the concave curvilinear surface is not too great such that the upper surface of the valve stem is too deep and therefore too difficult to adequately swab during cleaning/sterilization.

Preferably the slit formed in the valve stem is a generally straight through-slit as shown in U.S. Pat. No. 6,651,956 described above in which the slit is normally-closed when uncompressed but is forced tighter closed due to the compression of the valve stem when inserted into the valve body. Alternatively, the valve stem may comprise a normally-open slit, such as disclosed in U.S. Pat. No. 5,699,821, the disclosure of which is hereby incorporated by reference herein, which is then squeezed closed when the valve stem is inserted into the valve body.

In its most preferred embodiment with the surface having a concave radius, the valve may operate at increased back pressure than what would normally be achievable with a flat surface (e.g., an added 10 psi). It is believed that the increased back pressure is advantageously the result of the concave configuration over a flat configuration of the surface of the valve stem.

Finally, it is noted that unlike U.S. Pat. No. 8,221,363, the disclosure of which is hereby incorporated by reference herein, the reduced diameter portion of the valve stem comprises a generally circular cylindrical configuration that seals against the inner lumen of the valve body below the upper rim of the valve body such that, during collapsing, the reduced diameter portion of the valve stem moves inwardly into the valve body an appreciable distance as the slit begins to open.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 5A is a side plan view of the valve stem of the invention; FIG. 5B is a longitudinal cross-sectional view of FIG. 5A along lines A-A; FIG. 5C is an enlarged partial view of FIG. 5B; and FIGS. 5D and 5E are photographs of the swabable valve of the invention showing no lodging of the valve stem therein;

FIG. 6A is a side plan view of another embodiment of the valve stem of the invention; FIG. 6B is a longitudinal cross-sectional view of FIG. 6A along lines A-A; FIG. 6C is an enlarged partial view of FIG. 6B; and FIGS. 6D and 6E are photographs of the swabable valve of the invention showing no lodging of the valve stem therein;

FIG. 7 is an exploded view showing the arrangement of the valve stem of the invention in a valve;

FIG. 8A is a longitudinal cross-sectional view of one embodiment of the valve stem of the invention and FIG. 8B is an enlarged partial view thereof showing the configuration of the annular radius edge;

FIG. 9A is a longitudinal cross-sectional view of one embodiment of the valve stem of the invention and FIG. 9B is an enlarged partial view thereof showing the configuration of the annular chamfer;

Similar reference characters refer to similar parts throughout the several views of the drawings.

DETAILED DESCRIPTION OF THE PREFERRED EMBODIMENTS

Figure 1:
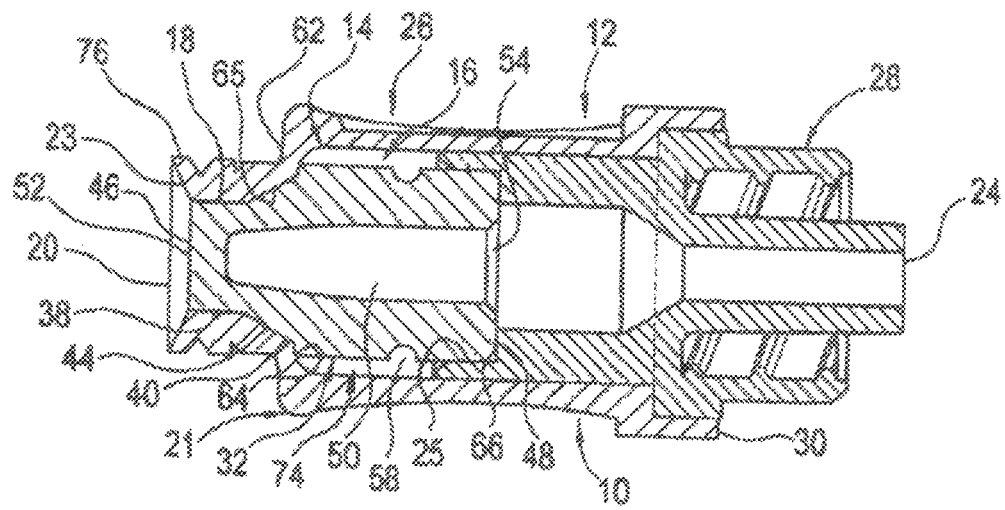
FIG. 1 is a cross-sectional view of a prior art swabable valve.
Figure 2:
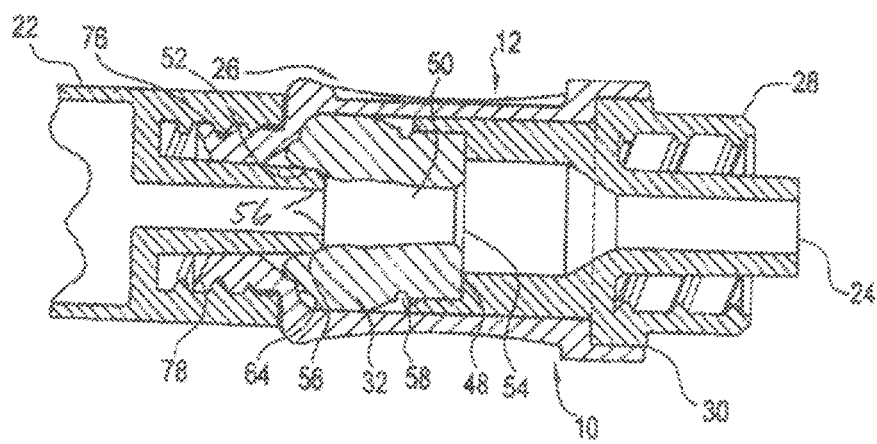
FIG. 2 is a cross-sectional view of the prior art swabable valve of FIG. 1 upon being accessed by an access device.
Figure 3A:
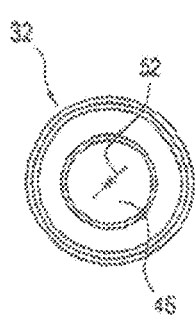
FIG. 3A is a top plan view of a prior art valve stem.
Figure 3B:
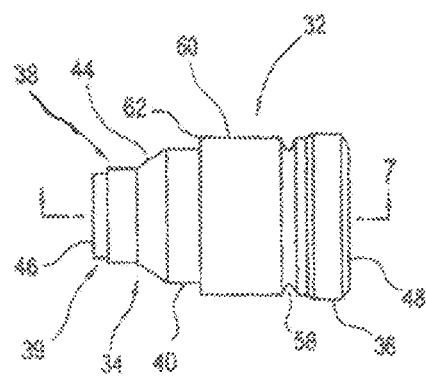
FIG. 3B is a side plan view thereof.
Figure 3C:
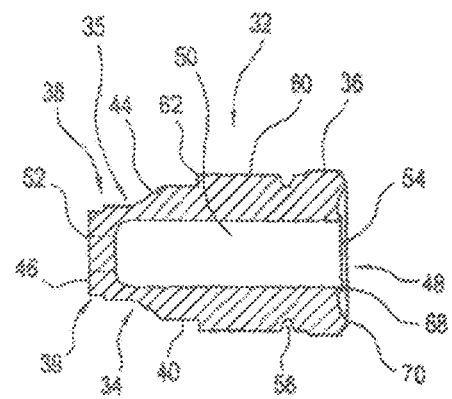
FIG. 3C is a longitudinal cross-sectional view thereof.
Figure 3D:
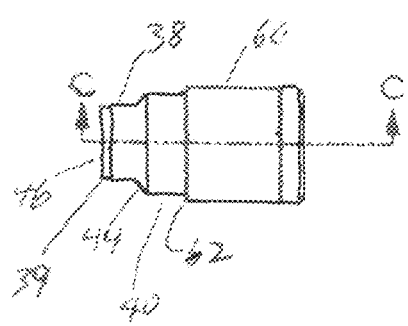
FIG. 3D is a top plan view of another prior art valve stem.
Figure 3E:
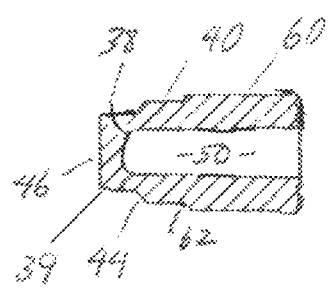
FIG. 3E is a longitudinal cross-sectional view thereof.
Figure 3F:
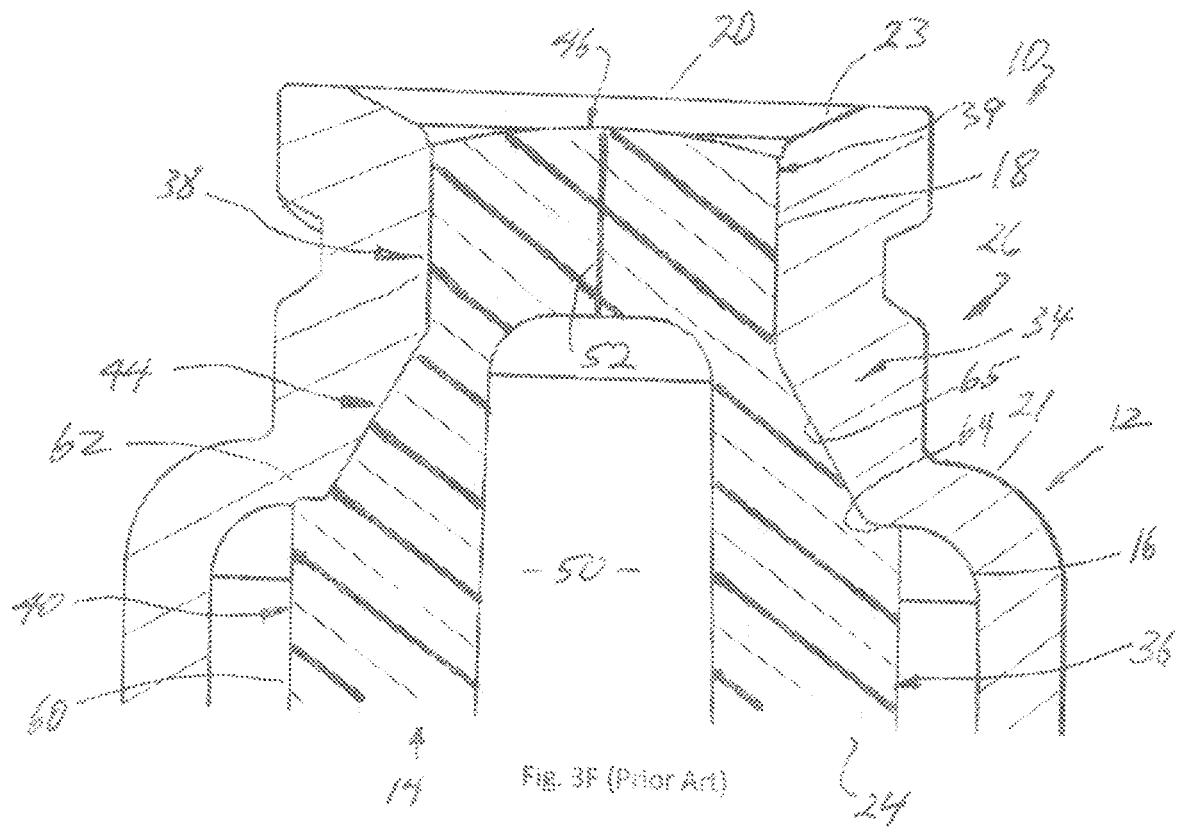
FIG. 3F is an enlarged partial longitudinal cross-sectional view of the prior art valve stem in a prior art valve body.
Figures 4A, 4B:
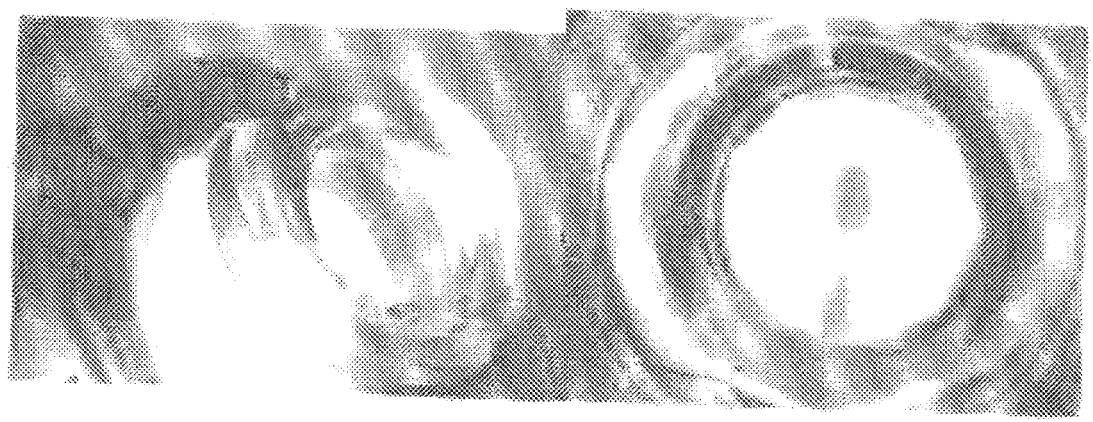
FIG. 4A is a photograph of the prior art swabable valve of FIG. 1 showing the valve stem lodged therein and FIG. 4B is a photograph of the prior art swabable valve of FIG. 1 showing the valve stem partially lodged therein.

The new preferred embodiments of the valve stem 100 are shown in FIGS. 5-11 and are intended to be used in connection with prior art or similar valve bodies 12 and rear body portions 28 (see exploded drawing of FIG. 7 showing arrangement of the new valve stem 100 in relation to a prior art valve body 12 and rear body portion 28). For clarity, the same reference numerals used in connection with features of the prior art valves 10 described above and shown in FIGS. 1-4 are used again in connection with the new preferred embodiments having the same features; however, new reference numerals are employed in connection with new features of the new preferred embodiments that differ from the corresponding features of prior art valves 10 in general and more specifically in regard to the prior art valve stems 32.

Referring to FIGS. 5A, 5B and 5C, one embodiment of the improved valve stem 100 of the invention comprises an exposed concave curvilinear surface 102 that is preferably formed at a concave radius (e.g., 0.208 inches) taken from the center line 104 of the valve stem 100 and extending rim-to-rim of the optional annular notch 39; it being understood that if the optional notch 39 is not employed, the concave curvilinear surface 102 extends rim-to-rim of the reduced diameter portion 38. As shown in FIGS. 5D and 5E, repeated engagement by an access device at various acute angles fails to lodge the valve stem 100 within the valve body 12; thereby assuring that the valve stem 100 always naturally returns to its properly-closed position.

It has been discovered that a curvilinear upper surface having a too long of a concave radius (e.g., 0.416 inches) extending rim-to-rim (see FIGS. 6A, 6B and 6C) thereby defining a shallower concave surface, could result in lodging of the valve stem 100 within the valve body 12 when the access device engages the valve stem 100 at an acute angle (see FIGS. 6D and 6E).

It is believed that there is a "sweet spot" of about a 0.208 inch radius for the concave curvilinear surface 102 at which the valve stem 100 will no longer lodge within the valve body 12 after being collapsed. Radiuses of a lesser amount may likewise preclude lodging; however, too short of a radius will deepen the concave surface 102 and will therefore increase the difficulty of swabbing the surface during cleaning and sterilizing.

More specifically, experiments have been conducted using groups of 40 durometer stems 100 at radiuses of 0.416, 0.208 and 0.125 inches. With valve stems 100 at the industry standard 40 durometer, the slits 52 of the 0.418 radius stems experienced partial lip collapses and some side collapses whereas the slits 52 of 0.125 radius stems 100 experienced some lip collapses. However, the slits 102 of the 0.208 radius stems 100 experienced no lip or side collapses. Hence, 40 durometer stems 100 with 0.208 radiuses appear to achieve the optimal results.

To determine the effect of changing the stem's 100 durometer from the industry standard of 40 durometer, additional experiments have been conducted using groups of 30 and 50 durometer stems 100 at the three radiuses of 0.416, 0.0.208 and 0.125 inches. The slits 52 of the 30 durometer stems 100 experienced lip or side collapses at each of the three radiuses whereas the 50 durometer stems 100 experienced some recessed stems (i.e., stems 100 that did not return fully after being accessed) and slits 52 with lip or side collapses. Hence, the industry standard 40 durometer stems 100 appear to achieve optimal results at the above-noted optimal radius of 0.208 inch radius.

As shown in FIGS. 8A and 8B, another embodiment of the improved valve stem 100 comprises an optional annular radius edge 110 extending about the periphery of the rim of the reduced-diameter portion 38 such that the exposed concave curvilinear surface 102 extends rim-to-rim from the inner rim of the radius edge 110 of the generally cylindrical reduced-diameter portion 38. The annular radius edge 100 serves a similar function to the optional annular notch 39 described above.

As shown in FIGS. 9A and 9B, another embodiment of the improved valve stem 100 comprises an optional annular chamfer 120 extending about the periphery of the rim of the reduced-diameter portion 38 such that the exposed concave curvilinear surface 102 extends rim-to-rim from the inner rim of the chamfer 120 of the generally cylindrical reduced-diameter portion 38. The chamfer 120 serves a similar function to the optional annular notch 39 described above.

Figure 10:
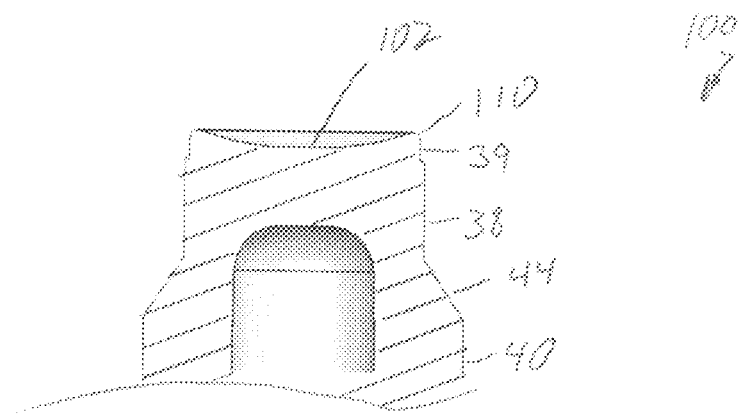
FIG. 10 is a partial cross-sectional view of one embodiment of the valve stem of the invention wherein the annular notch comprises an annular radius edge.
Figure 11:
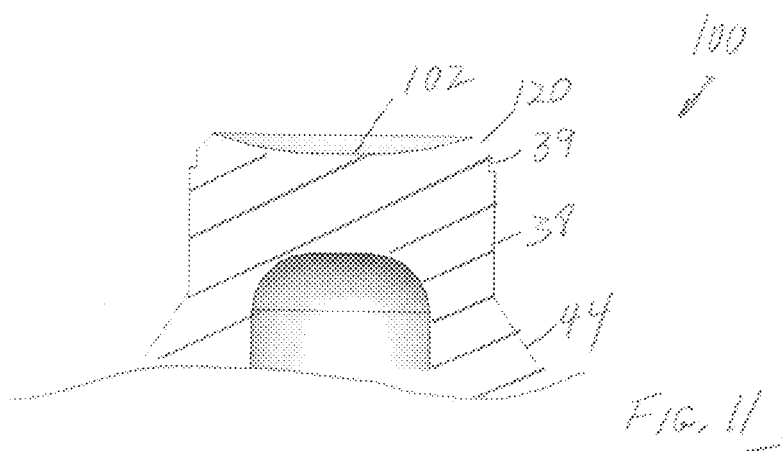
FIG. 11 is a partial cross-sectional view of one embodiment of the valve stem of the invention wherein the annular notch comprises an annular chamfer.

As shown in FIG. 10, when the optional annular notch 39 is employed, the annular radius edge 110 extends from the annular notch 39 such that the exposed concave curvilinear surface 102 extends rim-to-rim from the inner rim of the radius edge 110 of the annular notch 39 of the generally cylindrical reduced-diameter portion 38. Likewise, as shown in FIG. 11, when the optional annular notch 39 is employed, the annular chamfer 120 extends from the annular notch 39 such that the exposed concave curvilinear surface 102 extends rim-to-rim from the inner rim of the chamfer 120 of the annular notch 39 of the generally cylindrical reduced-diameter portion 38.

The present invention includes that contained in the appended claims as well as that of the foregoing description. Although this description has been described in its preferred form with a certain degree of particularity, it should be understood that the present disclosure of the preferred form has been made only by way of example and that numerous changes in the details of construction, combination, or arrangement of parts thereof may be resorted to without departing from the spirit and scope of the invention.

Now that the invention has been described,

What is claimed is:

1. A swabable valve (10) comprising a valve stem (100) that collapses into a valve body (12), said valve body (12) including a generally cylindrical reduced diameter section (18) having a generally circular rim, said valve stem (100) having a generally cylindrical reduced diameter portion (38) that extends fully into said cylindrical reduced diameter section (18) of said valve body (12), said cylindrical reduced diameter portion (38) including a through-slit (52) that opens when said valve stem (100) collapses into said valve body (12), said valve stem (100) having a concave curvilinear surface (102) that is substantially flush with said circular rim of said cylindrical reduced diameter section (18) of said valve body (12) when said valve stem (100) is not collapsed into said valve body (12); said concave curvilinear upper surface (102) of said valve stem (100) extending rim-to-rim within said cylindrical reduced diameter section (18) of said valve body (12).

2. The swabable valve (10) as set forth in claim 1, wherein said reduced diameter portion (38) further comprises an annular radius edge (110) extending about the periphery of the rim of the reduced-diameter portion (38) such that the concave curvilinear surface (102) extends rim-to-rim from an inner rim of the radius edge (110) of the generally cylindrical reduced-diameter portion (38).

3. The swabable valve (10) as set forth in claim 2, wherein said reduced diameter portion (38) further comprise an annular notch (39) and wherein said annular radius edge (110) extends about the periphery of the rim of the annular notch (39) such that the concave curvilinear surface (102) extends rim-to-rim from an inner rim of the radius edge (110) of the annular notch (39).

4. The swabable valve (10) as set forth in claim 1, wherein said reduced diameter portion (38) further comprises an annular chamfer (120) extending about the periphery of the rim of the reduced-diameter portion (38) such that the exposed concave curvilinear surface 102 extends rim-to-rim from an inner rim of the chamfer (120) of the generally cylindrical reduced-diameter portion (38).

5. The swabable valve (10) as set forth in claim 4, wherein said reduced diameter portion (38) further comprise an annular notch (39) and wherein said annular chamfer (120) extends about the periphery of the rim of the annular notch (39) such that the concave curvilinear surface (102) extends rim-to-rim from an inner rim of the chamfer (120) of the annular notch (39).

6. The swabable valve (10) as set forth in claim 1, wherein said concave curvilinear upper surface (102) of said valve stem (100) comprises a radius that is sufficient to prevent said valve stem (100) from becoming lodged within said valve body (12) upon collapsing thereby assuring that said valve stem (100) will return to non-collapsed position with said concave curvilinear surface (102) substantially flush with said circular rim of said cylindrical reduced diameter section (18) of said valve body (12).

7. The swabable valve (10) as set forth in claim 1, wherein said radius of said concave curvilinear surface (102) is not too great such that said concave curvilinear surface (102) of said valve stem (100) is too deep within said circular rim of said cylindrical reduced diameter section (18) of said valve body (12) and therefore too difficult to adequately swab.

8. The swabable valve (10) as set forth in claim 1, wherein said through-slit (52) formed in said valve stem (100) comprises a generally straight through-slit (52).

9. The swabable valve (10) as set forth in claim 1, wherein said through-slit (52) formed in said valve stem (100) is normally-closed when uncompressed but is forced tighter closed due to the compression of said valve stem (100) when inserted into said valve body (12).

10. The swabable valve (10) as set forth in claim 1, wherein said through-slit (52) formed in said valve stem (100) comprises a normally-open slit (52) which is then squeezed closed when said valve stem (100) is inserted into said valve body (12).

* * * * *